United States Patent [19]

McCall

[11] Patent Number: 4,944,937

[45] Date of Patent: Jul. 31, 1990

[54] COSMETIC STICKS

[75] Inventor: Patrick C. McCall, Cincinnati, Ohio

[73] Assignee: The Procter & Gamble Company, Cincinnati, Ohio

[21] Appl. No.: 683,829

[22] Filed: Dec. 19, 1984

[51] Int. Cl.$^5$ .................... A61K 7/32; A61K 7/34; A61K 7/38; A61K 7/42
[52] U.S. Cl. .................... 424/65; 424/DIG. 5; 424/59; 424/60; 424/66; 424/67; 424/68
[58] Field of Search .................... 424/DIG. 5, 65

[56] References Cited

U.S. PATENT DOCUMENTS

| | | |
|---|---|---|
| 3,196,079 | 1/1965 | Blaustein .................... 424/69 |
| 3,255,082 | 6/1966 | Barton .................... 424/68 |
| 4,126,679 | 11/1978 | Davy et al. .................... 424/66 |
| 4,137,306 | 1/1979 | Rubino et al. .................... 424/68 |
| 4,151,272 | 4/1979 | Geary et al. .................... 424/68 |
| 4,164,563 | 8/1979 | Chang .................... 424/83 |
| 4,229,432 | 10/1980 | Geria .................... 424/68 |
| 4,275,054 | 6/1981 | Sebag et al. .................... 424/DIG. 5 |
| 4,280,994 | 7/1981 | Turney .................... 424/68 |
| 4,336,246 | 6/1982 | Pekarek .................... 424/DIG. 5 |
| 4,379,136 | 4/1983 | Mochida .................... 424/65 |
| 4,381,293 | 4/1983 | Michel .................... 424/DIG. 5 |
| 4,414,200 | 11/1983 | Murphy et al. .................... 424/DIG. 5 |
| 4,435,382 | 3/1984 | Shin et al. .................... 424/66 |

FOREIGN PATENT DOCUMENTS

| | | |
|---|---|---|
| 117070 | 8/1984 | European Pat. Off. .................... 424/68 |
| 2852988 | 6/1979 | Fed. Rep. of Germany ... 424/DIG. 5 |
| 55-81810 | 6/1980 | Japan .................... 424/63 |
| 0081810 | 6/1980 | Japan .................... 424/DIG. 5 |
| 57-109706 | 7/1982 | Japan .................... 424/DIG. 5 |
| 542734 | 1/1942 | United Kingdom .................... 424/DIG. 5 |
| 1341618 | 12/1973 | United Kingdom .................... 424/68 |
| 2013085 | 8/1979 | United Kingdom .................... 424/DIG. 5 |

*Primary Examiner*—Dale R. Ore
*Attorney, Agent, or Firm*—David L. Suter; Steven J. Goldstein; Gretchen R. Hatfield

[57] ABSTRACT

Cosmetic stick compositions comprising one or more liquid base materials, one or more solidfying agents for the liquid base materials, and from about 2% to about 30% (by total composition volume) of chemically inert particulates of at least 10 microns in diameter and having a density less than about 0.60 g/ml. The liquid base materials are typically present at a level of from about 10% to about 90% (by total composition weight), and the solidifying agent is typically present at a level of from about 3% to about 70% (by total composition weight). These cosmetic sticks may be of a gel stick type or a wax stick type, depending upon the particular liquid base materials and solidifying agents used. Preferred cosmetic sticks contain a safe and effective amount of an active material having, for example, antiperspirant or deodorant activity.

20 Claims, No Drawings

COSMETIC STICKS

BACKGROUND OF THE INVENTION

The present invention relates to stick-type cosmetic compositions. More particularly, it relates to improved antiperspirant sticks.

The chemical and cosmetic literature is replete with formulations of stick-form cosmetics for various uses, such as antiperspirants, deodorants, and lipsticks. The specific stick formulation may vary depending upon such factors as the intended use, the "active" ingredient to be incorporated, and the part of the body to which the product is to be applied.

There are three main types of such cosmetic stick formulations: compressed powder sticks, gel sticks, and wax sticks. While each of these formulation types may have advantages in certain use situations, each also has disadvantages. For example, compressed powder sticks are often brittle and hard, and leave a cosmetically-unacceptable dust upon application. Gels may be unstable due to evaporation of alcohol or (in antiperspirant sticks) due to interaction of astringent metal salts with the soaps present. Wax-based formulations can also yield cosmetically-unacceptable products due to such factors such as hardness, greasiness, and stickiness.

The use of powders and particulates has been disclosed in the literature in order to modify the cosmetic and formulation characteristics of stick-type products. For example, polyethylene in a powder base has been disclosed for use in stick-form powder cosmetics in Japanese Patent specification No. 57-109,706, published July 8, 1982. Similarly, U.S. Pat. No. 4,379,136, Mochida, issued Apr. 5, 1983, discloses polyethylene as a binding aid in compressed powder cosmetic sticks. Inert powders, such as polystyrene, have also been used in gel stick formulations, as disclosed in U.S. Pat. No. 3,255,082, Barton, issued June 7, 1966. Powder materials are disclosed in a matrix of insoluble alcohols and volatile silicone oils, so as to form wax-based cosmetic sticks, in U.S. Pat. No. 4,126,679, Davy, et al., issued Nov. 21, 1978.

It has now been discovered that gel or wax-based stick cosmetic compositions, containing certain chemically inert particulates of a defined size and of low density, have superior application and in-use characteristics when compared to similar cosmetic sticks not having such particles. In particular, wax cosmetic sticks of this invention incorporating astringent metal salts have improved application characteristics, such as "glide", as well as improved in-use characteristics, such as tackiness and appearance.

SUMMARY OF THE INVENTION

The present invention provides solid cosmetic stick compositions comprising:
(a) one or more liquid base materials;
(b) a solidifying agent of a type and amount effective to solidify said liquid base materials; and
(c) from about 2% to about 30% (by total composition volume) of chemically inert particles of at least about 10 microns in diameter and having a density less than about 0.60 g/ml.

The liquid base materials are typically present at levels of from about 10% to about 90% (by total composition weight), and the solidifying agent is typically present at levels of from about 3% to about 70% (by total composition weight). This invention also provides cosmetic sticks, further comprising from about 10% to about 70% (by weight) of one or more astringent metallic salts, particularly useful as antiperspirants.

DESCRIPTION OF THE INVENTION

The cosmetic sticks of this invention contain three essential ingredients: liquid base materials, solidifying agents, and chemically inert particles of a defined size and of low density. These compositions (herein "cosmetic sticks") encompass any solid (or semi-solid) composition intended for human use in order to deposit material on human tissue. Thus, the instant cosmetic sticks preferably contain additional ingredients, depending upon their intended use, such as antiperspirant salts and deodorizing compounds. These essential and optional ingredients must be "cosmetically-acceptable", i.e., safe for human use and aesthetically acceptable at the levels at which such materials are used in the present compositions, at a reasonable risk/benefit ratio.

Specifically, the cosmetic sticks of the present invention comprise:
(a) one or more liquid base materials;
(b) a solidifying agent of a type and amount effective to solidify said liquid base materials; and
(c) from about 2% to about 30% (by volume) of chemically inert particles of at least about 10 microns in diameter and having a density less than about 0.60 g/ml.

The liquid base materials are typically present at levels of from about 10% to about 90% (by weight). The solidifying agent is typically present at levels of from about 3% to about 70% (by weight). (As used herein percentages "by volume" are with respect to total composition volume; percentages "by weight" are with respect to total composition weight. In addition, such percentages "by volume" of the chemically inert particulates are determined with respect to the actual volume occupied by the particulates in the final composition, as a function of the weight and the true density of the particular particulate material used.) These cosmetic sticks can be generally described as being either gel sticks or wax sticks, depending upon the particular liquid base materials and solidifying agent used. The preferred levels of the components of these sticks will, accordingly, vary depending upon the type of stick desired. Further, the specific liquid base materials and solidifying agents, as well as the preferred materials, will vary according to the type of stick and the desired rheologic properties.

ESSENTIAL COMPONENTS

Liquid Base Materials:

The cosmetic sticks of this invention contain one or more liquid materials, herein "liquid base materials", that form the base matrix of the solid stick when combined with a suitable solidifying agent. (As used herein, "liquid" materials are those that are liquid at ambient conditions.) As is appreciated by those skilled in the art, the selection of a particular liquid base material, as well as the selection of a suitable solidifying agent, will vary depending upon the particular type of cosmetic stick desired. Such "types" of sticks can generally be classified as either gel sticks or wax sticks. A variety of liquid base materials and solidifying agents among those useful herein, as well as sticks made from these materials, are described in the following documents, all incorporated by reference herein: S. Plechner, "Antiperspirants and Deodorants", 2 *Cosmetics, Science and Technology*, 373–416 (M. Balsam and E. Sagarin ed. 1972); C. Fox, "Gel and Sticks Review and Update", 99 *Cosmetics and Toiletries* 19–52 (1984); N. Geria, "Formulation of Stick Antiperspirants and Deodorants", 99 *Cosmetics and Toiletries,* 55–99 (1984); and "Gels and Sticks Formulary", 99 *Cosmetics and Toiletries*, 77–87 (1984). The present cosmetic sticks may also be multi-phase sticks, such as the multi-phase sticks disclosed in U.S. Pat. No. 4,120,948, Shelton, issued Oct. 17, 1978 (incorporated by reference herein) and U.S. Pat. No. 4,202,879, Shelton, issued May 13, 1980 (incorporated by reference herein).

The wax cosmetic sticks of this invention preferably contain from about 20% to about 60% (by weight) of a liquid base material. The liquid base materials useful in these wax sticks generally also serve as emollients, improving the cosmetic acceptability of the cosmetic stick. Accordingly, the liquid base materials useful in the wax-based cosmetic sticks of the present invention are preferably organic non-hydrocarbon materials that are liquid and substantially water-insoluble. (As used herein, the term "water-insoluble" refers to water solubility less than about 1.0% at 20° C.) Such liquid base materials are disclosed in the following patent documents, all incorporated by reference herein: U.S. Pat. No. 4,049,792, Elsnau, issued Sept. 20, 1977; U.S. Pat. No. 4,151,272, Geary, et al., issued Apr. 24, 1979; U.S. Pat. No. 4,229,432, Geria, issued Oct. 21, 1980; and U.S. Pat. No. 4,280,994, Turney, issued July 28, 1981. Preferred liquid base materials useful in the present wax sticks are described in U.S. Pat. No. 4,126,679, Davy, et al., issued Nov. 21, 1978 (incorporated by reference herein) and European Patent Specification No. 117,070, May, published Aug. 29, 1984 (incorporated by reference herein).

Such organic non-hydrocarbon liquid base materials include fatty acid and fatty alcohol esters, water-insoluble ethers and alcohols, polyorganosiloxanes, and mixtures thereof. Fatty acid and fatty alcohol esters useful herein include isopropyl myristate, isopropyl palmitate, cetyl acetate, cetyl propionate, di-n-butyl phthalate, diethyl sebacate, diisopropyl adipate, and ethyl carbomethyl phthalate. Isopropyl myristate, isopropyl palmitate, di-n-butyl phthalate, and mixtures thereof, are among the preferred fatty acid and fatty alcohol esters useful herein. Water-insoluble ethers useful herein include polypropylene glycol and the condensation products of an alkylene oxide with an alcohol. A preferred water-insoluble ether is the condesation product of about 14 moles of propylene oxide with one mole of butyl alcohol, sold as Fluid AP$^R$ by Union Carbide.

The wax sticks of this invention preferably contain from about 35% to about 60%, more preferably from about 40% to 60% (by weight), of a polyorganosiloxane as the liquid base material. The polyorganosiloxanes useful herein may be cyclic or linear, and are preferably volatile silicone oils. (As used herein, "volatile" refers to those materials which have a measurable vapor pressure at ambient conditions.) A description of various volatile silicones is found in Todd, et al., "Volatile Silicone Fluids for Cosmetics", *Cosmetics and Toiletries*, 91, 27–32 (1976), incorporated by reference herein. Preferred cyclic silicones include the polydimethylsiloxanes containing from about 3 to about 9 silicon atoms, preferably containing from about 4 to about 5 silicon atoms. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes. Examples of silicone oils useful in the present invention include: Dow Corning 344, Dow Corning 345, and Dow Corning 200 (manufactured by the Dow Corning Corporation); Silicone 7207 and Silicone 7158 (manufactured by the Union Carbide Corporation); SF1202 (manufactured by General Electric); and SWS-03314 (manufactured by Stouffer Chemical).

The gel sticks of the present invention preferably contain from about 6% to about 80%, preferably from about 15% to about 30% (by weight), of a liquid base material. The liquid base materials useful in these gel sticks may be selected to also provide desirable cosmetics, such as emolliency or a cooling sensation when applied to the skin. Liquid base materials useful herein include water, lower monohydric alcohols, polyhydric alcohols, and mixtures thereof. Among these base materials are ethanol, isopropanol, n-propanol, n-butanol, isobutanol, tert-butyl alcohol, ethylene glycol, propylene glycol, trimethylene glycol, glycerine, 1,3-butane diol, 1,4-butane-diol, and mixtures thereof. Such liquid base materials are disclosed in the following patent documents, all incorporated by reference herein: U.S. Pat. No. 2,900,306, Slater, issued Aug. 18, 1959; U.S. Pat. No. 3,255,082, Barton, issued June 7, 1966; U.S. Pat. No. 4,137,306, Rubino, et al., issued Jan. 30, 1979; U.S. Pat. No. 4,154,816, Roehl, et al., issued May 15, 1979; U.S. Pat. No. 4,226,889, Yuhas, issued Oct. 7, 1980; U.S. Pat. No. 4,346,079, Roehl, issued Aug. 24, 1982; U.S. Pat. No. 4,383,988, Teng, et al., issued May 17, 1983; European Patent Specification No. 107,330, Luebbe, et al., published May 2, 1984; and U.S. patent application Ser. No. 630,790, DiPietro, filed July 13, 1984. Preferred liquid base materials useful in the present gel sticks are described in European Patent Specification No. 24,365, Sampson, et al., published Mar. 4, 1981 (incorporated by reference herein).

Solidifying Agents:

The cosmetic sticks of this invention contain one or more materials, herein singly or collectively referred to as a "solidifying agent", that are effective to solidify the particular liquid base materials to be used in the cosmetic stick. (As used herein, the term "solidify" refers to the physical and/or chemical alteration of the liquid base material so as to form a solid or semi-solid at ambient conditions, i.e., to form a final composition which has a stable physical structure and is deposited on the skin during normal use conditions.) As is appreciated by those skilled in the art, the selection of the particular solidifying agent for use in the cosmetic stick will depend upon the particular type of stick desired, i.e., gel or wax-based, the desired rheology, the liquid base material used and the other materials to be used in the composition.

The wax cosmetic sticks of this invention preferably contain from about 5% to about 50% (by weight) of a material having wax-like characteristics as a solidifying agent. Such waxy materials may also serve as emollients. Among the waxy materials useful herein are the high melting point waxes, i.e., having a melting point of from about 65° C. to about 102° C., such as beeswax, spermaceti, carnauba, baysberry, candelilla, montan, ozokerite, ceresin, paraffin, synthetic waxes such as Fisher-Tropsch waxes, microcrystalline wax, and mixtures thereof. Ceresin, ozokerite, white beeswax, synthetic waxes, and mixtures thereof, are among the preferred high-melting point waxes useful herein. Compositions containing waxes among those useful herein are disclosed in U.S. Pat. No. 4,049,792, Elsnau, issued Sept. 20, 1977 (incorporated by reference herein). Low melting waxes, having a melting point of from about 37° C. to about 75° C., are preferred for use in the wax sticks of this invention. Wax sticks of this invention, which contain volatile silicone oils as a liquid base material, preferably contain from about 10% to about 35%, more preferably from about 10% to about 20% (by weight), of a low-melting wax. Such materials include fatty acids, fatty alcohols, fatty acid esters and fatty acids amides, having fatty chains of from about 8 to about 30 carbon atoms, and mixtures thereof. Preferred wax-like materials include cetyl alcohol, palmitic acid, stearyl alcohol, behenamide, sucrose esters of tallow fatty acids, mono and di-fatty acid esters of polyethylene glycol, and mixtures thereof. Stearyl alcohol, cetyl alcohol, and mixtures thereof, are particularly preferred. Fatty acids, fatty alcohols, and other wax-like materials useful in this invention are also disclosed in the following U.S. Patents, all incorporated by reference herein: U.S. Pat. No. 4,151,272, Geary, et al., issued Apr. 24, 1979; U.S. Pat. No. 4,229,432, Geria, issued Oct. 21, 1980; and U.S. Pat. No. 4,280,994, Turney, issued July 28, 1981. Preferred wax-like materials useful as solidifying agents in the present wax sticks are described in U.S. Pat. No. 4,126,679, Davy, et al., issued Nov. 21, 1978 (incorporated by reference herein). Preferred mixtures of wax-like materials comprise fatty alcohols containing carbon chains of from about 14 to about 18 carbon atoms, and alcohols having chain lengths of 20 carbons or longer, wherein the final mixture contains from about 1% to about 3% (by weight) of the longer-chain fatty alcohols. Compositions containing these fatty alcohol mixtures are described in European Patent Specification No. 117,070, May, published Aug. 29, 1984 (incorporated by reference herein).

The gel sticks of this invention preferably contain from about 3% to about 30%, preferably from about 3% to about 10% (by weight), of a solidifying agent. The particular amount of solidifying agent to be used will depend upon the particular solidifying agent and the liquid base material used, and the desired physical characteristics of the gel stick. Solidifying agents useful in the gel sticks of this invention are, in general, surface-active compounds which form networks immobilizing or solidifying the liquid base materials into a gel. Such solidifying agents include: soaps, such as the sodium and potassium salts of higher fatty acids, i.e., acids having from 12 to 22 carbon atoms; amides of higher fatty acids; higher fatty acid amides of alkylolamines; dibenzaldehyde-monosorbitol acetals; alkali metal and alkaline earth metal salts of the acetates, propionates and lactates; waxes, such as candelilla and carnauba waxes; and mixtures thereof. Among those solidifying agents preferred for use in the gel sticks of this invention are sodium stearate, sodium palmitate, aluminum stearate, and mixtures thereof. Gel stick compositions containing solidifying agents among those useful herein are described in the following patent documents, all incorporated by reference herein: U.S. Pat. No. 2,900,306, Slater, issued Aug. 18, 1959; U.S. Pat. No. 3,255,082, Barton, issued June 7, 1966; U.S. Pat. No. 4,137,306, Rubino, et al., issued Jan. 30, 1979; U.S. Pat. No. 4,154,816, Roehl, et al., issued May 15, 1979; U.S. Pat. No. 4,226,889, Yuhas, issued Oct. 7, 1980; U.S. Pat. No. 4,346,079, Roehl, issued Aug. 24, 1982; U.S. Pat. No. 4,383,988, Teng, et al., issued May 17, 1983; European Patent Specification No. 107,330, Luebbe, et al., published May 2, 1984; and U.S. patent application Ser. No. 630,790, DiPietro, filed July 13, 1984. Preferred solidifying agents useful in the present gel sticks are described in European Patent Specification No. 24,365 Sampson, et al., published Mar. 4, 1981 (incorporated by reference herein).

Chemically Inert Particulates:

The cosmetic sticks of this invention contain from about 2% to about 30%, preferably from about 3% to about 20%, more preferably from about 6% to about 13% (by volume), of chemically inert particulates of at least about 10 microns in diameter and having a density less than about 0.60 g/ml (grams/milliliter). Preferably, the chemically inert particulates have a density of from about 0.02 to about 0.50 g/ml. (As used herein, the term "density" refers to true density of discrete particulates, as opposed to bulk density.) Cosmetic sticks with large particulates may have a cosmetically unacceptable "gritty" feel. Hence, preferably the particulates do not exceed about 150 microns in diameter. Most preferably, the particulates are from about 15 microns to about 75 microns in diameter. Commercially-available particulate materials useful herein may be of a non-uniform size distribution, containing some particles outside the size ranges described herein. For the purposes of this invention, such non-uniform materials must have a median diameter within the ranges described herein.

Particulates may be spherical or irregular in shape. Spherical particles are particularly preferred. Irregularly shaped particles, useful in the present invention, are of at least 10 microns in minimum diameter or width. Preferably, then, such irregularly shaped particles do not exceed 150 microns in maximum diameter or length.

As used herein, "chemically inert" particulates are those particulates comprised of materials or mixtures of materials which neither melt nor decompose nor react with the liquid base materials, solidifying agents or the other components of the instant cosmetic sticks, under the conditions of preparation or of use. Materials of a density greater than about 0.60 g/ml may be used in chemically inert particulates that are of a hollow configuration, such that the overall particle density is within the ranges described herein. Among the particulate materials that may be incorporated in the instant invention include those comprised of silicates, polyolefins (such as polystyrene, polyethylene, and polypropylene), nylon, Teflon$^R$, thermoplastics (such as polymethyl methacrylate, polyacrylonitrile, polyvinyl chloride, polyvinylidene chloride, and polystyrene), and mixtures thereof.

Chemically inert particulates useful herein are commercially available from a variety of sources. A preferred particulate material is comprised of hollow borosilicate spheres, such as those manufactured by 3M Company. Such particulates have diameters of approximately 10 to 60 microns, and densities of from 0.15 to 0.40 g/ml. Other preferred chemically-inert particulates useful herein are hollow plastic spheres, such as those disclosed in the following documents, all incorporated by reference herein: U.S. Pat. No. 2,797,201, Veatch, et al., issued June 25, 1957; U.S. Pat. No. 3,515,569, Walters, et al., issued June 2, 1970; U.S. Pat. No. 3,615,972, Morehouse, Jr., et al., issued Oct. 26, 1971; U.S. Pat. No. 4,006,273, Wolinski, et al., issued Feb. 1, 1977; and British Patent Specification No. 1,103,472, published Feb. 14, 1968. Such a particularly preferred hollow spherical chemically-inert material useful herein is sold by Pierce and Stevens Company, under the name Miralite. These Miralite particulates typically have diameters of approximately 10 to 60 microns, and a density of about 0.03 g/ml. On a weight basis, such microspheres are usually incorporated in the present sticks at levels of from about 0.06% to about 1%, preferably from about 0.1% to about 0.6%, more preferably from about 0.2% to about 0.4%.

NON-ESSENTIAL COMPONENTS

Optional "Non-Active" Components:

The compositions of this invention preferably contain optional components which modify the physical characteristics of the cosmetic sticks. Such components include hardeners, strengtheners, emollients, colorants, perfumes, emulsifiers, and fillers. Optional components, useful herein, are disclosed in the following patent documents, all incorporated by reference herein: U.S. Pat. No. 3,255,082, Barton, issued June 7, 1966; U.S. Pat. No. 4,049,792, Elsnau, issued Sept. 20, 1977; U.S. Pat. No. 4,137,306, Rubino, et al., issued Jan. 30, 1979; U.S. Pat. No. 4,279,658, Hooper, et al., issued July 14, 1981; U.S. patent application Ser. No. 630,790, DiPietro, filed July 13, 1984; and European Patent Specification No. 117,070, May, published Aug. 29, 1984.

In particular, the instant compositions preferably contain from about 1% to about 20% (by weight) of an emollient. One type of preferred emollient, that is suitable for use in the wax-based sticks of this invention, is the non-volatile silicone oils. Dimethicone is a particularly preferred non-volatile silicone oil for such use. These materials may also serve a similar function as the liquid base materials useful herein. Such emollients suitable for use in the present solid stick compositions include fatty acid and fatty alcohol esters and water insoluble ethers, such as those disclosed in U.S. Pat. No. 4,202,879, Shelton, issued May 13, 1980 (incorporated by reference herein). Other emollients include the propylene oxide condensation products containing from about 5 to about 35 propylene oxide units. Examples of such emollients include Fluid AP$^R$ (a condensate of about 14 moles of propylene oxide with about 1 mole of butyl alcohol) sold by Union Carbide, and a polypropylene glycol having a molecular weight of about 1200. U.S. Pat. No. 4,280,994, Turney, issued July 28, 1981 (incorporated by reference herein) discloses polyethylene glycols having a molecular weight of from about 950 to about 1600, for use in antiperspirant stick compositions.

The instant cosmetic sticks may also contain from about 0.5% to about 10% (by weight) of an inert filler material. Suitable filler materials include talc, colloidal silica (such as Cab-O-Sil, sold by Cabot Corp.), clays (such as bentonite), and mixtures thereof. The use of such fillers as stabilizing agents in cosmetic sticks is disclosed in U.S. Pat. No. 4,126,679, Davy et al., issued Nov. 21, 1978 (incorporated by reference herein).

The cosmetic sticks of the present invention may also include perfumes, emulsifiers, and coloring agents. These components are preferably present at levels from about 0.1% to about 2.0% (by weight).

Optional "Active" Components:

Preferred embodiments of the instant cosmetic sticks contain a safe and effective amount of one or more components, herein "active components", which are meant to be deposited upon human tissue. Active components include astringents, bacteriostats, fungistats, pigments, dyes, colorants, perfumes, emollients, ultra violet absorbers, and mixtures thereof. The active components must be stable in the formulations of the instant invention. A "safe and effective" amount of an active component is that amount which yields the desired benefit at a reasonable benefit/risk ratio for human usage. Various active components among those useful in this invention are described in U.S. Pat. No. 4,226,889, Yuhas, issued Oct. 7, 1980 (incorporated by reference herein).

Particularly preferred embodiments of the present invention are useful as antiperspirants. Thus, antiperspirant sticks, according to the present invention, additionally comprise a safe and effective amount of an antiperspirant material, i.e., a compound or composition having antiperspirant activity. Astringent metallic salts are preferred antiperspirant compounds, and may be incorporated in the instant compositions at levels of from about 10% to about 70%, preferably from about 15% to about 50%, most preferably from about 15% to about 40% (by weight).

Preferred astringent metallic salts include the inorganic and organic salts of aluminum, zirconium and zinc, and mixtures thereof. Particularly preferred are the aluminum and zirconium salts, such as aluminum halides, aluminum hydroxyhalides, zirconyl oxyhalides, zirconyl hydroxyhalides, and mixtures thereof. Such metal salts, and complexes thereof, are described in European Patent Specification No. 117,070, May, published Aug. 29, 1984 (incorporated by reference herein) and U.S. Pat. No. 4,137,306, Rubino, et al., issued Jan. 30, 1979 (incorporated by reference herein).

Preferred aluminum salts include those of the formula

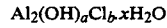

$$Al_2(OH)_aCl_b \cdot xH_2O$$

wherein a is from about 2 to about 5; $a+b=6$; x is from about 1 to about 6; and wherein a, b, and x may have non-integer values. Particularly preferred are aluminum chlorhydroxides referred to as "5/16 basic chlorhydroxide", wherein $a=5$, and "⅔ basic chlorhydroxide," wherein $a=4$. Processes for preparing aluminum salts are disclosed in the following documents, all incorporated by reference herein: U.S. Pat. No. 3,887,692, Gilman, issued June 3, 1975; U.S. Pat. No. 3,904,741, Jones, et al., issued Sept. 9, 1975; U.S. Pat. No. 4,359,456, Gosling, et al., issued Nov. 16, 1982; and British Patent Specification No. 2,048,229, Fitzgerald, et al., published Dec. 10, 1980. Mixtures of aluminum salts are described in British Patent Specification No. 1,347,950, Shin, et al., published Feb. 27, 1974 (incorporated by reference herein) and U.S. patent application No. 546,806, Thurston, et al., filed Oct. 31, 1983 (incorporated by reference herein).

Zirconium salts are also preferred for use in antiperspirant sticks of the present invention. Such salts are of the general formula

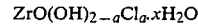

$$ZrO(OH)_{2-a}Cl_a \cdot xH_2O$$

wherein a is from about 1 to about 2, preferably from about 1.5 to about 1.87; x is from about 1 to about 7; and wherein a and n may have non-integer values. These zirconium salts are disclosed in Belgium Patent No. 825,146, Schmitz, issued Aug. 4, 1975 (incorporated by reference herein). Particularly preferred zirconium salts are those complexes also containing aluminum and glycine, commonly known as "ZAG complexes". Such ZAG complexes contain aluminum chlorhydroxide and zirconyl hydroxychloride of the formulae detailed above. These compounds in ZAG complexes are disclosed in U.S. Pat. No. 3,679,068, Luedders, et al., issued Feb. 12, 1974 (incorporated herein by reference), and U.S. Pat. No. 4,120,948, Shelton, issued Oct. 17, 1978 (incorporated by reference herein).

As is appreciated by those skilled in the art, certain of the antiperspirant materials described above may be ineffective in, or lead to instability of, the gel sticks of this invention. Accordingly, antiperspirant sticks of this invention are preferably wax sticks. However, certain antiperspirant materials may be incorporated in gel sticks of this invention, particularly including the alcohol-soluble aluminum salts. Gel-type antiperspirant sticks are described in the following U.S. Patents, all incorporated by reference herein: U.S. Pat. No. 3,255,082, Barton, issued June 7, 1966; U.S. Pat. No. 4,137,306, Rubino, et al., issued Jan. 30, 1979; and U.S. Pat. No. 4,383,988, Teng, et al., issued May 17, 1983.

Cosmetic sticks of the present invention may also include a safe and effective amount of deodorant materials, such as bacteriocides and fungicides, or mixture thereof. Such deodorant materials are usually present at levels of from about 0.1% to 1.0% (by weight). Suitable deodorants include bacteriostatic quaternary ammonium compounds such as cetyl-trimethyl ammonium bromide, cetyl pyridinium chloride, benzethonium chloride, diisobutyl phenoxy ethoxy ethyl dimethyl benzyl ammonium chloride, sodium N-lauryl-sarcosine, sodium N-polymethyl sarcosine, lauroyl sarcosine, N-myristoyl glycine, potassium N-lauroyl sarcosine, stearyl trimethyl ammonium chloride, and mixtures thereof. Other suitable deodorant materials include 2,4,4'-trichloro-2'hydroxydiphenyl ether and sodium bicarbonate. Certain of the astringent salts useful herein may also serve as deodorant materials. For example, sodium aluminum chlorhydroxy lactate, sold as Chloracel$^R$ by Reheis Chemical Company, is useful as a deodorant material.

METHODS

The present invention encompasses methods of preparing cosmetic stick compositions with improved in-use performance characteristics. These methods generally comprise adding chemically inert particles, of a defined size and density, to a stick base consisting of liquid base materials and a solidifying agent, yielding a cosmetic stick comprised as described above. In a preferred embodiment, this invention provides a method of reducing the in-use stickiness while enhancing the application characteristics of antiperspirant sticks.

The cosmetic sticks of this invention can be made using techniques well known in the art. Such techniques, among those generally useful herein, are described in "Gels and Sticks Formulary", 99 *Cosmetics and Toiletries* 77-87 (1984), incorporated by reference herein. Due to the low density of the chemically inert particulates useful herein, care must be taken in handling these materials in order to avoid excess dustiness during manufacture. Further, the formulation of the present cosmetic sticks may require additional precautions, such as agitation and careful control of the temperature of the molten stick formulation prior to solidification, so as to maintain even distribution of the instant chemically inert particulate materials throughout the product. One particularly preferred method of manufacturing wax-based sticks of the present invention is to slurry or otherwise combine the chemically-inert particulates with the liquid base materials prior to stick formulation.

The following non-limiting examples illustrate the compositions, processes and uses of the present invention.

EXAMPLE I

An antiperspirant stick, according to the instant invention, was made comprising:

| Component | % (by weight) |
| --- | --- |
| cyclomethicone | 53.97 |
| stearyl alcohol | 13.00 |
| castor wax | 4.00 |
| cetyl alcohol | 2.00 |
| Miralite 177* | 0.30 |
| ZAG complex** | 26.70 |
| perfume | 0.03 |

*polyvinylidene chloride hollow microsphere particulates, of approximately 35 microns mean diameter and 0.036 g/ml density, sold by Pierce & Stevens Chemical Corp., present at a level of about 9.2% (by volume)
**zirconium-aluminum-glycine-hydroxy chloride astringent complex, sold by Reheis Chemical Company The stearyl alcohol, castor wax and cetyl alcohol were heated together at approximately 77° C., and mixed with approximately one-half of the cyclomethicone. The Miralite was slurried into the remaining quantity of cyclomethicone and added to the wax/cyclomethicone mixture, maintaining the resulting mixture at a temperature greater than 82° C. The ZAG active material and perfume were then added. The material was thoroughly mixed at a temperature of 85° C., allowed to cool to approximately 53° C., and poured into stick-forms. Solid antiperspirant sticks were then formed upon cooling below approximately 50° C.

An antiperspirant stick, formulated as above, was applied to the underarm of a human subject, reducing the perspiration in the applied area of the subject. In the above example, stearyl alcohol, palmitic acid, behenamide, sucrose esters of tallow fatty acids, and mono and di-fatty acid esters of polyethylene glycol are substituted for cetyl alcohol, respectively, with substantially similar results.

EXAMPLE II

An antiperspirant stick, according to the present invention, is made comprising:

| Component | % (by weight) |
| --- | --- |
| cyclomethicone | 60.0 |
| stearyl alcohol | 11.7 |
| castor wax | 5.0 |
| Miralite 177* | 0.5 |
| Chlorhydrol Micro-Dry** | 22.0 |
| fragrance | 0.8 |

*present at a level of about 15.3% (by volume)
**5/6 basic aluminum chlorhydrate astringent, sold by Reheis Chemical Company

EXAMPLE III

An antiperspirant stick, according to the present invention, was made comprising:

| Component | % (by weight) |
| --- | --- |
| cyclomethicone | 53.82 |

-continued

| Component | % (by weight) |
|---|---|
| stearyl alcohol | 13.00 |
| cetyl alcohol | 1.10 |
| myristyl alcohol | 1.10 |
| castor wax | 3.50 |
| 3M Glass Bubbles* | 0.75 |
| ZAG Complex | 26.70 |
| fragrance | 0.3 |

*soda-lime-borosilicate hollow glass spheres of from 5 to 60 microns (average 27 microns) in diameter and density of approximately 0.22 g/ml, sold by 3M Company present at a level of about 3.8% (by volume)

EXAMPLE IV

A deodorant stick, according to the present invention, is made comprising:

| Component | % (by weight) |
|---|---|
| ethanol | 70.8 |
| propylene glycol | 17.0 |
| water | 2.5 |
| sodium stearate | 7.5 |
| Miralite 181* | 0.2 |
| zinc phenol sulfonate | 1.0 |
| coloring | 0.2 |
| fragrance | 0.8 |

*polyvinylidene chloride hollow microsphere particulates in water wet form, of from 10 to 60 microns in diameter and a density of approximately 0.032 g/ml, sold by Pierce & Stevens Chemical Corp., present at a level of 6.9% (by volume)

All of the components listed above, except for the Miralite, are mixed together, under reflux conditions, at about 82° C. until all materials are melted and dissolved. The Miralite particulate is then slurried into the mixture and stirred. The mixture is then cooled to about 71° C., while maintaining agitation, and poured into stick forms. A deodorant gel stick is formed upon cooling.

EXAMPLE V

An antiperspirant stick, according to the present invention, is made comprising:

| Component | % (by weight) |
|---|---|
| Fluid AP$^R$* | 35.8 |
| cetyl alcohol | 10.0 |
| ozokerite wax | 8.5 |
| 3M Glass Bubbles** | 1.9 |
| aluminum chlorhydroxide | 43.0 |
| fragrance | 0.8 |

*condensation product of one mole of butyl alcohol with 14 moles of propylene oxide, sold by Union Carbide Corporation
**present at a level of about 9.5% (by volume)

In the above example, stearyl alcohol, myristyl alcohol, lauryl alcohol and glycerol monostearate are substituted, respectively, for cetyl alcohol, with substantially similar results. Also, isopropyl myristate, isopropyl palmitate and polypropylene glycol are substituted for Fluid AP, respectively, with substantially similar results. Ceresin, white beeswax, spermaceti, carnauba, bayberry, candelilla, montan and paraffin are also substituted, respectively, for ozokerite, with substantially similar results.

EXAMPLE VI

A deodorant stick, according to the present invention, is made comprising:

| Component | % (by weight) |
|---|---|
| Fluid AP$^R$ | 44.01 |
| propylene glycol | 20.00 |
| ethanol | 8.50 |
| sodium stearate | 6.25 |
| 3M Glass Bubbles* | 0.64 |
| di-isopropyl adipate | 10.00 |
| myristyl alcohol | 8.00 |
| stearyl trimethyl ammonium chloride | 0.30 |
| coloring | 1.30 |
| fragrance | 1.00 |

*present at a level of about 2.6% (by volume)

In the above example, ethylene glycol, trimethylene glycol and glycerine are substituted, respectively, for propylene glycol, with substantially similar results. Also, sodium palmitate and aluminum monostearate are substituted for sodium stearate, respectively, with substantially similar results.

EXAMPLE VII

A cosmetic stick, according to the present invention, is made comprising:

| Component | % (by weight) |
|---|---|
| cyclomethicone | 44.55 |
| dimethicone | 20.00 |
| cetyl alcohol | 15.00 |
| myristyl alcohol | 10.00 |
| beeswax | 4.50 |
| Miralite 177* | 0.95 |
| zinc oxide | 5.00 |

*present at a level of about 26.0% (by volume)

The cosmetic stick formed as described above is useful as an ultra violet absorbing sunscreen.

What is claimed is:
1. A cosmetic stick composition, comprising:
   (a) one or more liquid base materials;
   (b) a solidifying agent of a type and amount effective to solidify said liquid base materials; and
   (c) from about 2% to about 30% (by volume) of chemically inert particulates of at least about 10 microns in diameter and having a density less than about 0.60 g/ml.
2. A cosmetic stick composition, according to claim 1, wherein said liquid base materials are present at a level of from about 10% to about 90% (by weight).
3. A cosmetic stick composition, according to claim 2, wherein said solidifying agent is present at a level of from about 3% to about 70% (by weight).
4. A cosmetic stick composition, according to claim 3, wherein said chemically inert particulates are present at a level of from about 3% to about 20% (by volume).
5. A cosmetic stick, according to claim 1, wherein said chemically inert particulates are from about 15 to about 75 microns in diameter.
6. A cosmetic stick, according to claim 5, wherein said chemically inert particulates have a density of from about 0.02 to about 0.50 g/ml.
7. A cosmetic stick, according to claim 6, wherein said chemically inert particulates are hollow silicate spheres.
8. A cosmetic stick, according to claim 6, wherein said chemically inert particulates are hollow plastic spheres.

9. A cosmetic stick, according to claim 3, additionally comprising from about 1% to about 20% (by weight) of an emollient.

10. A cosmetic stick, according to claim 3, additionally comprising a safe and effective amount of an active component.

11. A cosmetic stick, according to claim 10, which is a gel stick.

12. A cosmetic stick, according to claim 10, which is a wax stick.

13. A cosmetic stick, according to claim 11, wherein said active component is a deodorant material present at a level of from about 0.1% to about 1.0% (by weight).

14. A cosmetic stick, according to claim 12, wherein said active material is an antiperspirant material present at a level of from 10% to about 70% (by weight).

15. A cosmetic stick composition, in gel form, comprising:
   (a) from about 15% to about 30% (by weight) of polyhydric alcohol;
   (b) from about 3% to about 10% (by weight) of a soap; and
   (c) from about 3% to about 20% (by volume) of chemically inert particulates, of from about 15 to 75 microns in diameter, having a density of from about 0.02 to 0.50 g/ml.

16. A cosmetic stick comprising in gel form, according to claim 15, additionally comprising from about 0.1% to about 1% of a deodorant.

17. A cosmetic stick composition in gel form, according to claim 15, additionally comprising a monohydric alcohol.

18. A cosmetic stick composition in wax form, comprising:
   (a) from about 10% to about 65% (by weight) of one or more volatile silicone oils;
   (b) from about 10% to about 70% (by weight) of one or more materials having wax-like characteristics; and
   (c) from about 3% to about 20% (by volume) of chemically inert particulates, of from about 15 to 75 microns in diameter, having a density of from about 0.02 to about 0.50 g/ml.

19. A cosmetic stick in wax form, according to claim 18, additionally comprising from about 10% to about 70% of an antiperspirant material.

20. A cosmetic stick in wax form, according to claim 18, wherein said waxy materials are selected from the group consisting of fatty acids, fatty alcohols, fatty acid esters and fatty acid amides, having fatty chains of from about 8 to about 30 carbon atoms, and mixtures thereof.

* * * * *